United States Patent [19]
Wilson et al.

[11] Patent Number: 4,578,185
[45] Date of Patent: Mar. 25, 1986

[54] WASTE DISPOSAL SYSTEM

[75] Inventors: Joseph H. Wilson, Indianapolis; Jeffrey C. Rapp, Greenwood; Brian K. Southern, Zionsville; Martin E. Elliott, Indianapolis, all of Ind.

[73] Assignee: Medical Safetec, Inc., Indianapolis, Ind.

[21] Appl. No.: 758,439

[22] Filed: Jul. 24, 1985

[51] Int. Cl.[4] .............................. B01D 36/00
[52] U.S. Cl. ..................... 210/85; 210/143; 210/171; 210/173; 210/192; 210/202; 210/251; 210/297; 210/401
[58] Field of Search ............... 210/143–145, 210/147, 148, 153, 158, 160, 171, 173, 174, 188, 192, 202, 251, 259, 297, 298, 346–401, 138–140, 85, 87–89, 91, 92, 488–492

[56] References Cited

U.S. PATENT DOCUMENTS

| | | | |
|---|---|---|---|
| 3,334,749 | 8/1967 | Ladd | 210/145 |
| 3,504,794 | 4/1970 | Tholl et al. | 210/145 X |
| 3,939,077 | 2/1976 | Seibert | 210/401 |
| 3,965,006 | 6/1976 | Otte | 210/148 X |
| 4,032,446 | 6/1977 | Miller, Jr. | 210/173 |
| 4,070,290 | 1/1978 | Crosby | 210/91 |
| 4,110,218 | 8/1978 | Marriott et al. | 210/259 X |
| 4,233,157 | 11/1980 | Miller | 210/143 X |
| 4,268,388 | 5/1981 | Romeo | 210/259 X |
| 4,340,473 | 7/1982 | Lindman et al. | 210/173 |
| 4,427,157 | 1/1984 | Klein | 210/401 X |

Primary Examiner—Thomas Wyse
Attorney, Agent, or Firm—Dick and Harris

[57] ABSTRACT

A waste disposal system for treating and disposing of infectious waste articles in a substantially controlled, closed, aseptic environment and for converting such infectious waste articles into a safely disposable, non-infectious non-toxic residue of solid waste independent from disinfecting liquid waste. A waste delivery conveyor transfers waste articles from an input region to preliminary waste processing apparata for preliminarily fragmenting the waste for further treatment by the system. Disinfectant spray is deposited on the waste as it enters the preliminary waste processing apparatus with the fragments resulting therefrom, together with the disinfectant liquid, being transferred to rotary hammermill elements to convert the fragment disinfectant solution to a solution of fine waste particles and disinfectant solution. Liquid solid particle separator apparata then separates the solid waste particles from the liquid disinfectant for independent evacuation of same. The system further includes vacuum ventilation elements to maintain any released bacteria or particles within the system until completely processed and disinfected with system switching controls serving to operate and sequence operation of the system components relative to one another by computer.

37 Claims, 13 Drawing Figures

WASTE DISPOSAL SYSTEM

BACKGROUND OF THE INVENTION

The present invention relates, in general, to waste management facilities and in particular to a waste disposal system for treating and disposing of infectious waste articles in a substantially controlled, closed, aseptic environment for conversion of same into independent safely disposable non-infectious, non-toxic solid waste residues and independent liquids.

Within the last fifteen years, emphasis has been directed towards the design of waste disposal treatment methods and systems which more effectively deal with the complex problems associated with treating and disposing of the many glassware, needles, syringes and substantially hazardous waste discarded from a hospital environment, for example, together with the highly infectious tissues, test tubes, slides, etc. that accompany such hazardous products in a medical or research facility. Over the years, on-site incinerators with their associated high costs of operation and ineffective utilization of costly resources such as natural gas, petroleum and the like, have been utilized to dispose of such dangerous and infectious waste on a bulk basis, while adversely affecting the environment through the release of potentially toxic exhaust and vapors emanating from incineration of, for example, plastics used in substantial volumes within such facilities.

During the above more recent years, several systems and apparata have been developed which may be utilized to process, on a relatively small scale, portions of the waste articles which emanate from hospital, research and experimental facilities while, generally, not being capable of disposing and permanently treating, for safe release into sewerage or land fill, most, if not all of the articles contemplated for trash or discard in such an environment. Indeed, U.S. Pat. No. 3,926,379 covering a syringe disintegrator discloses such a "specialized" disposal apparatus in which hypodermic syringes may be pulverized and disinfected for subsequent disposal. The assignee of the present invention, through its pending applications, Ser. Nos. 06/541,140 filed Oct. 12, 1983 and 06/658,701 filed Oct. 9, 1984 disclose yet additional systems for disintegrating some forms of hospital waste.

The present invention is directed towards a waste disposal system capable of accepting, processing and effectively disposing of virtually all the waste materials a present facility is typically desirous of discarding, in a non-furnace environment without the need for incineration—a system in which all the waste is "neutralized" so as to be safe, after processing, for sewerage or land fill release through mechanical alteration of the waste articles and treatment with disinfectants which, in combination more effectively obviate the need for incineration.

It is accordingly an object of the present invention to provide a waste disposal system which more effectively disintegrates and fragments a vast majority of disposable materials as to make them noninfectious and capable of subsequent disposal via conventional sewerage and land fill techniques.

It is an additional object of the present invention to accept large volumes of waste materials of virtually any composition typically found in a hospital, medical, experimental or laboratory environment, for disinfection and disposal of same—in an environment where disintegration is optomized for complete disinfection.

It is also an object of the present invention to provide for such a waste disposal system in which disinfectant itself may be generated on a on-site basis at reduced costs in an environment where detergents are not needed so as avoid impairing the effect of the disinfectant used during the disposal treatment operations.

As an additional object of the present invention is the provision of a waste disposal system that mechanically disintegrates the majority of discarded materials from such an "infectious" environment to substantially small particulate components for complete disinfection of same, where immediately prior to disposal of the byproducts of said treatment, the solid waste and liquid disinfectant components developed during processing are separated through an effective new liquid-solid separation technique for bulk utilization.

As a further object of the present invention is the provision of a waste disposal system which relies upon preliminary fragmentation of the waste materials, followed by subsequent violent disintegration of the remaining fragmented particles for complete envelopment within disinfectant solution, and for substantial impregnation thereof, while safely maintaining the immediately surrounding environment free of bacterialaden air or particles carried by the air within the system. The system further treats and releases such air maintained within the system through a series of filters so as to yield all by-products of the disposal process safe to personnel both inside and outside the facility, and to the environment in general.

These and other objects of the invention will become apparent in view of the present specification, claims and drawings.

SUMMARY OF THE INVENTION

The present invention comprises a waste disposal system for treating and disposing of infectious waste articles in a substantially controlled, aseptic environment as well as a system for converting this infectious waste into a safely disposable, nontoxic, non-infectious residue through disintegration and disinfection techniques.

The system includes input means into which accumulated quantities of waste articles are initially placed for subsequent treatment and disposal of same. From the system input means the waste is delivered from a first delivery end to a second delivery end positioned substantially opposite to the first delivery end. Preliminary waste processing means are located proximate to this second delivery end of the waste delivery means for preliminarily restructuring the waste articles into substantially small waste fragments for further treatment and disposal of same by the waste disposal system.

Also located proximate to the second end of the waste delivery means and proximate to the preliminary waste processing means are disinfectant spray means for dispensing a disinfectant liquid used to envelop and impregnate the waste articles and waste fragments towards disinfection of existing bacteria within the waste articles themselves and the preliminarily restructured waste fragments. The envelopment and impregnation of the disinfectant liquid into the waste articles themselves is assisted firstly by the force of the spray as well as by the preliminary processing operation which firstly fragments the pieces, as well as by other portions of the disposal system which, in disintegrating the waste articles into smaller and smaller particles serves to assist in their disinfection by the disinfecting liquid.

The disinfecting liquid solution and waste fragments pass from the preliminary waste processing means by fragment solution channeling means having a first and second end, with its first end proximate to the preliminary waste processing means and its second end operably attached to a rotary hammermill means. This rotary hammermill is capable of receiving the waste fragment-disinfectant solution from the fragment solution channel for the purpose of violently disintegrating these waste article fragments at a substantially high speed in the substantially liquid environment of the disinfectant solution, so as to create a waste particle-disinfectant solution. The rotary hammermill means are powered by hammermill motor means operably coupled thereto, and emanating from the hammermill itself is a hammermill particle-solution transmission apparatus having a first and second end through which the waste particle disinfectant solution is routed out of the rotary hammermill for further treatment by the waste disposal system.

From the rotary hammermill the substantially disintegrated waste particle disinfectant solution passes through a liquid solid particle separation means operably attached to the hammermill transmission means for separating, on a continuous basis, the disintegrated particles of solid waste from any excess enveloping and impregnating disinfectant liquid. This liquid solid particle separator includes operable connections to liquid evacuation means and solid particle evacuation means for disposal of the disinfectant liquid and solid waste particles separately from one another.

The waste disposal system further includes system vacuum ventilation means operably associated with the system's component segments or "stations" for effectively precluding the inadvertent release of bacteria and/or other contamination during the treatment and disposal of waste articles by the system. Furthermore, system switching control means are operably associated with one or more of the waste input means, waste delivery means, preliminary waste processing means, disinfectant spray means, rotary hammermill means, liquid solid particle separation means and system vacuum ventilation means, to control the activation and sequencing of one or more of these structural components relative to the other co-operating components.

In one embodiment of the invention the waste disposal system includes a disinfectant storage facility for containing accumulated quantities of disinfectant liquid. This disinfectant storage means is operably connected to the disinfectant spray means for supplying, through appropriate liquid conduits, desired amounts of disinfectant liquid for spraying of same onto the waste articles at the abovesaid position adjacent one or more of the second delivery end of the waste delivery means and the preliminary waste processing means. It is further contemplated in this embodiment that the invention additionally includes disinfectant generation means which generates a disinfectant solution containing sodiumhypochlorite and water. In such an embodiment, the disinfectant generation means comprises an on-site disinfectant generator operably coupled to the disinfectant storage means by additional disinfectant conduit, by creating for storage the sodiumhypochlorite compound which is created through electrolytic processing of a brine solution. Furthermore, in this embodiment, the generated sodiumhypochlorite solution is stored after generation, in disinfectant storage means, after which it is combined with water to form a two tenths (0.2%) percent concentrate solution, having a pH of 8.5, for subsequent supply to the spraying means, as needed.

In the preferred embodiment of the invention the waste delivery means comprises a substantially inclined motorized conveyor apparatus which has, at its first delivery end, a system input means integrated thereinto for initial placement of the quantities of waste articles for subsequent treatment and disposal. This conveyor apparatus further includes a substantially flat, continuous conveyor belt with laterally positioned bars thereupon for effectively transferring waste articles to the second delivery end, proximate the preliminary waste processing means, as a driving motor operably attached to the conveyor apparatus is activated by the system's switching control means to transfer the waste articles riding upon the conveyor apparatus. Preferably, the laterally positioned bars and the conveyor apparatus itself are formed of a substantially elastomeric material such as urethane or rubber. Furthermore, in this preferred embodiment the conveyor apparatus includes one or more draped slitted curtains suspended immediately above the conveyor belt along its longitudinal path of movement. The slitted curtains permit an uninterrupted passage of the accumulated waste articles on the conveyor belt as the conveyor belt moves from the first delivery end to the second delivery end of the waste delivery means for subsequent carrying of the articles into the preliminary processing means.

The conveyor apparatus further includes substantially sealed conveyor housing above and about the conveyor belt from which the slitted curtains are suspended, the curtains co-operating with the housing to preclude the harboring, backflow and inadvertent release of potential particles or bacteria present in the system proximate to the waste delivery means and to reduce and isolate noise emanating from the rest of the system. It is contemplated that the one or more draped slitted curtains would be constructed of a substantially vinly material to more effectively enable smooth unobstructed passage of said waste articles past the slitted curtain as they move upwardly on the conveyor belt as well as to simplify the overall cleaning of the slitted curtain. Likewise, the conveyor apparatus housing enclosure would be constructed of a substantially stainless steel material, in the form of an enclosure chute, to preclude the undesired harboring of bacteria in the proximity of the waste delivery means.

With further regard to maintaining sanitary conditions proximate to the waste delivery means, in this preferred embodiment the system input means includes, at a position proximate the first delivery end, a drain located at the lowermost region of the conveyor apparatus to enable the draining of rinsing solution which may be used to rinse the waste delivery means and system input means between operations of the waste disposal system in order to wash away potential accumulation of errant disinfectant spray or infected or bacterial laden waste particles.

In the waste disposal system of the present invention, the preliminary waste processing means preferably comprises a dual element counter-rotating cutter-shredder apparatus. In such preliminary waste processing means each of the dual elements possesses a plurality of shredding disks in which each disk has three shredding teeth fashioned thereinto, with the disks sequentially articulated in alternating fashion between one another so that one element nests within the shredding disks of the other element. Associated with the cutting disks of the dual elements are a series of stationery jogging members operably disposed in sequential fashion within adjacent positions among the cutting disks. The cutter-shredder is powered and driven by a cuttershredder motor operably attached to each of the counter-rotating dual elements—a motor which preferably includes a torque reactive control in order to instantaneously react to overloads occuring within the cutter-shredder so as to be capable of deactiving and stopping the shredder in the event of a jam.

In this preferred embodiment, the preliminary waste processing means is operably disposed in a substantially sealed housing immediately surrounding the dual counter-rotating shredding elements. This shredder housing has, attached to its upper region, a substantially sealed chute element which operably communicates with the substantially sealed conveyor apparatus housing formed about the waste delivery means. The sealed chute element receives the accumulated waste articles at said second delivery end of the waste delivery means to in turn transfer same, through gravity, to the nip formed between the dual element counter-rotating shredder disks in the preliminary waste processing means. In this same embodiment, the spray means comprise a substantially horizontally spray bar extending the axial length of the dual elements and fixedly restrained in position thereover for substantially showering the disinfectant liquid from its position along the top of the sealed chute with a vertically downward orientated spray. This disinfectant spray serves to continuously dispense disinfectant over the accumulated quantities of waste articles as the articles reach the second delivery end, while the waste articles fall by gravity into the shredder-cutter apparatus as well as while the waste articles await and enter the fragmentation process performed by the shredder-cutter —continuously bathing even the waste fragments released from the preliminary processing means into the fragment solution channeling means leading to the rotary hammermill. Preferably, the sprayer means dispenses the liquid disinfectant spray at a rate approximating thirty gallons per minute onto the waste articles and the waste article fragments located therebelow.

In the preferred embodiment of the invention, the rotary hammermill means comprises a high speed hammermill apparatus capable of violently disintegrating the waste article fragments created by the preliminary processing means, mixing them with the enveloping and impregnating disinfectant liquid solution so as to effectively disintegrate the fragments into relatively small waste particles for improved penetration and impregnation by the liquid disinfectant. This in turn enables the complete and substantial disinfection of bacteria carried by such waste articles.

In order to channel the fragment-liquid solution from the preliminary waste processing means, solution channeling means in a form of a substantially sealed channel member are operably connected in a sealed relationship to the sealed preliminary waste processing housing surrounding the preliminary waste processing means. At the first end of the channeling means the fragment-liquid solution is received by the channeling means for transferring same, through both gravity and ejection from the shredder, to a side entry aperture in the rotary hammermill housing at the second end of the fragment solution channeling means. The rotary hammermill itself is disposed within a sealed hammermill housing through which the hammermill motor is operably coupled to the hammermill apparatus disposed therewithin, with the entry aperture fabricated at an axially offset position into the side wall of this sealed hammermill housing.

The hammermill apparatus itself comprises a primary rotating member directly and operably connected to the hammermill motor through a hammermill axle. A plurality of hammer members are operably mounted for pivotal movement about the outer periphery of the primary rotating member and these hammers, together with the plurality of fragment jogging members operably positioned at the upper interior periphery of the hammermill apparatus housing, co-operate to effectively disintegrate the waste article fragments received from the preliminary processing means upon rotation of the primary member and hammer members of the hammermill. Additionally, a plurality of apertures are located at and through the bottom peripheral region of the hammermill housing for releasing the waste particle-disinfectant solution after disintegration of same by said rotary hammermill means—releasing said solution into the first end of the hammermill transmission means. These release apertures include a plurality of substantially small circular release apertures leading through the hammermill housing as well as an overload release aperture maintained in a normally sealed position during normal operation of the hammermill by a releasable covering door operably connected to door positioning means. The door positioning means are capable of opening the covering door and overload release aperture when speed detection means disclose a jam within the hammermill apparatus so as to expedite the release of accumulated waste particle-disinfectant solution out of the rotary hammermill apparatus and into the hammermill transmission means. Preferably, the speed detection means comprises a rotary speed sensor positioned about the hammermill axle for detecting an abrupt reduction in speed to, in turn, activate the covering door to immediately open, to more rapidly evacuate the waste particle-disinfectant solution from the interior of the hammermill apparatus housing. The door positioning means comprises a pneumatically operated piston operably affixed at one end of the covering door to operate same upon the occurrence of a jam while maintaining same in a normally closed position at all other times.

The primary rotating member of the hammermill apparatus is suspended for rotation within opposite faces of the hammermill housing by a plurality of hammermill bearing assemblies operably communicating with the primary rotating member through the hammermill axle. Each of the plurality of hammermill bearing assemblies has means for withstanding contamination arising out of the migration of waste particle disinfectant solution emanating from within the hammermill housing and along the axle, potentially into portions of the bearing, so as to preclude corrosion and interference of the migrating particles-solution with the bearing.

In the preferred embodiment, the means for withstanding contamination in each bearing assembly comprises the utilization of at least one bearing spacer means immediately adjacent each of the bearing assemblies with the bearing spacers coming in direct and operably communication with respective portions of the axle. An inlet and an outlet fitting positioned in each of the bearing spacers permits attachment thereto of an incoming and outgoing flushing conduit respectively for operable communication with the interior of the spacer itself.

Flushing medium may then be pumped through the flushing conduits to enter into and exit from the bearing spacer. This flushing medium is pumped continuously during the operation of the hammermill apparatus to flush each bearing spacer to, in turn, clean out portions of migrating waste particles and disinfectant solution which could otherwise enter and adversely affect the bearing assemblies themselves. In this embodiment it is contemplated that the bearing assembly further comprise a slinger element operably and fixedly attached to the axle within each bearing spacer for further assisting in the centrifugal dispersion of the flushing medium so as to further beneficially assist the flushing of migrating waste particles and disinfectant solution out of each bearing spacer and through and out of the exiting flushing conduit.

Another embodiment of means for withstanding contamination in the bearing assemblies comprises a continuous greasing apparatus operably and fixedly attached to the bearing elements within each bearing assembly which, under pressure, intermittently and effectively circulates fresh greasing medium into and about the bearing elements. This accordingly assists in precluding the inadvertent contamination, corrosion and undesired creation of excess friction about the rotating bearing element by constantly greasing same while further flushing out traces of migrating waste particles and disinfectant solution reaching such rotating elements.

In the preferred embodiment also the rotary hammermill motor means are operably connected to the primary rotating member within the hammermill housing through a quick-release coupling apparatus means which automatically releases the motor means from its connection with the primary rotating member upon the occurrence of a torque limiting jam. Upon the occurrence of such a jam, the change in rotating speed of the hammermill is sensed to activate the quick release coupling operably communicating with the hammermill. The quick release coupling disconnects the motor means from the hammermill apparatus upon the occurrence of such a jam and, automatically, assists the motor to "wind down" to avoid a free riding motor situation after such a disconnection. The quick release coupling further includes features capable of warning and notifying the operator of the waste disposal system of the occurrence of the motor disconnection and wind down.

From the bottom of the hammermill and particularly the release apertures, the waste particle-liquid solution enters the hammermill transmission means comprising a substantially sealed chute assembly in operable and sealed communication with the hammermill housing operably surrounding the hammermill, so as to transfer the particle-liquid solution from the hammermill at the transmission means first end to the liquid-solid particle separation means at the second end of the hammermill transmission means.

In the preferred embodiment, the liquid solid particle separation means comprises a substantially sealed particle separator housing operably attached in sealed fashion to the second end of the hammermill transmission. At the attachment region there exists a particle separator entry aperture through which the disintegrated particles of solid waste and the enveloping-impregnating disinfectant liquid jointly enter the particle separator for separation therebetween. Continuous conveyor sieve means are operably positioned immediately adjacent the particle separator entry aperture for collecting the solid particle-liquid solution therefrom and for separating excess quantities of the disinfectant liquid from the solid waste particles.

Preferably, the conveyor sieve comprises a substantially continuous looped conveyor element formed by a plurality of interlocking articulated separator belt components. Each such separator belt component includes means for attachment to its immediately adjacent equivalently structured separator belt component as well as a substantially planar surface for supporting the solid waste particles. Additionally a plurality of slotted apertures are formed through these components through which the disinfectant liquid may pass downwardly towards collection adjacent the liquid evacuation means. The conveyor sieve is powered by separator motor means to collect the waste particle-liquid solution on a continuous basis from the hammermill transmission means, with the conveyor sieve itself positioned in a substantially upwardly inclined orientation to deliver the solid waste particles to the solid particle evacuation means and direct the flow of the separated disinfectant liquid to the liquid evacuation means for subsequent independent disposal of same, respectively. Preferably, the separator belt components are possessed of slotted apertures of a size capable of releasing the majority of disinfectant liquid mixed with the solid waste particles thereupon while being substantially incapable of releasing any substantial volumes of solid waste particles therethrough so as to substantially direct most of the solid waste particles to the solid waste particle evacuation means.

In the preferred embodiment also, the solid particle-liquid separation means includes routing plate means positioned between the upper and lower portions of the continuous conveyor sieve belt. This routing plate serves to direct the separated disinfectant liquid and particles small enough to pass through the slotted apertures in the separator belt components away from the backside of the lower portion of the conveyor sieve to a disposable position proximate to the liquid evacuation means. The liquid solid separator further includes conveyor sieve shoulder regions immediately proximate to the longitudinal edges of the conveyor sieve with brush elements positioned operably adjacent these longitudinal edges to further route the solid waste particles toward the solid waste particle evacuation means. The liquid solid particle separator further includes a scraper element positioned immediately adjacent the conveyor sieve at its uppermost climb proximate to the solid waste evacuation means to direct solid waste particles which may be adhering to the conveyor sieve, due to the existance of a small amount of liquid, so as to prompt same into the solid waste evacuation means.

Not only the solid waste particles-liquid solution from the hammermill is going into the liquid solid separation means. The solid waste particulate and impregnating disinfectant which are being flushed from the bearing spacers proximate to the hammermill bearing assemblies is also being routed into the liquid solid separator notwithstanding the relatively small amount of such contaminants being flushed in such a manner.

In the preferred embodiment of the invention the liquid evacuation means comprises a drain assembly operably communicating with the user's sanitary or sewage transmission line while the solid waste particle evacuation means comprises a storage container or receptacle such as a wheeled cart capable of accumulating the solid waste disintegrated particles prior to removal to an appropriate land fill facility. In this embodiment the solid waste particle evacuation means further includes a placement detection sensor operably associated therewith which serves to deactivate operation of the liquid-solid particle separator when the solid waste particle evacuation means or wheeled cart, for example, is out of position. A "cart-full" detector may also be utilized to disclose to the operator the need to replace a full cart with an empty one. Furthermore, it is contemplated that the liquid evacuation means may include evacuation filter means to preclude the undesired evacuation of potentially accumulatable solid waste particles directly through the liquid evacuation drain leading to the sewage lines. With such a small buildup of solid waste proximate to the liquid waste evacuation means it is contemplated that a screen or other filtering means can be changed at scheduled intervals by disposing of any additional solid waste particles at said position into the solid waste evacuation means relatively close thereto.

The system vacuum ventilation means comprises an operably connected series of housings about the waste delivery means, the preliminary waste processing means, the hammermill means, and liquid solid separation means which co-operate with the fragment solution channeling means, the hammermill solution transmission means and the one or more slitted draped curtains to form a substantially sealed uni-directional ventilation circuit. This ventilation circuit is attached at the liquid solid waste separator to fan exhaust means for circulating air within the ventilation circuit in said one direction through and out of same. The rotary hammermill itself further acts as a supplemental exhaust means to augment the uni-directional exhausting of potentially bacteria laden air therethrough at an exhaust rate less than that of the fan exhaust means to preclude the forced release of airborne contaminants emanating from the rotary hammermill. The air within the ventilation circuit is then directed from the system input means towards and through the liquid solid separator to in turn, be released from the fan exhaust means.

Preferably, the fan exhaust means further comprises two or more independent ventilation circuit extension means operably attached in a substantially sealed affixation to the solid liquid particle separator housing for channeling the air within the ventilation circuit therefrom. In this embodiment, filtering means are operably associated with each of the two or more independent ventilation circuit extension means to filter mists, vapors, waste particles and bacteria from the air prior to its release from the system. A blower apparatus is operably associated with each of the two or more independent ventilation circuit extension means for creating the uni-directional flow of the air, for driving the air through the filtering means and for ultimately discharging the filtered air from the waste disposal system.

In this embodiment additionally, the filtering means includes a plurality of filtering media to filter the mists, vapors, particles, etc. in the air. This plurality of media includes a hog hair, polyester, pleated and hepa filtering media to effectively filter the air prior to its release from the waste disposal system, preferably at a location external to the facility housing the present waste disposal system. Furthermore, in this embodiment, each such filtering means includes a filtering monitor to disclose the occurrence of filter saturation of each media element to, in turn, appropriately notify an operator so that a media element can be replaced.

The overall waste disposal system of the present invention includes system switching control means relying upon computer controlled switching and sequencing apparata. The computer controlled switching and sequencing apparata include monitors with diagnostic means to disclose switching control sequencing operations and problems as they occur, and further include indicia output means for disclosure of diagnostic messages. The switching control means further preferably includes a remote test switching apparatus capable of being physically relocated to any position along the waste disposal system to enable the remote isolated testing of any structural components by one operator, without assistance, while permitting simultaneous viewing of the results of the component testing by said single operator.

It is additionally contemplated that the invention further includes elastomeric mounting means operably interposed among the supporting structures for one or more of the waste delivery means, the preliminary waste processing means, the rotary hammermill means, the liquid solid particle separation means, the system vacuum ventilation means and system switching control means to effectively isolate and reduce the extent of vibration and noise emanating from same.

The invention further contemplates utilizing spray means 32 (or separate spray means) between machine operations to counter the corrosive effects of disinfectant on metallic machine parts such as the preliminary processing shredder. At the end of a machine operative period, prior to machine shut-down (after processing of all waste therethrough) a diluted mixture of disinfectant solution and water is sprayed, followed by a spray of just water and finally a solution of water soluble oil with water—to deposit a film of oil on such machine parts during extended down times of the system. This film of oil is removed upon startup of the system, by the disinfectant solution utilized in processing the waste.

DETAILED DESCRIPTION OF THE DRAWINGS

While this invention is susceptable of embodiment in many different forms, there is shown in the drawings and will herein be described in detail, one specific embodiment, with the understanding that the present disclosure is to be considered as an examplification of the principles of the invention and is not intended to limit the invention to the embodiment illustrated.

Figure 1:
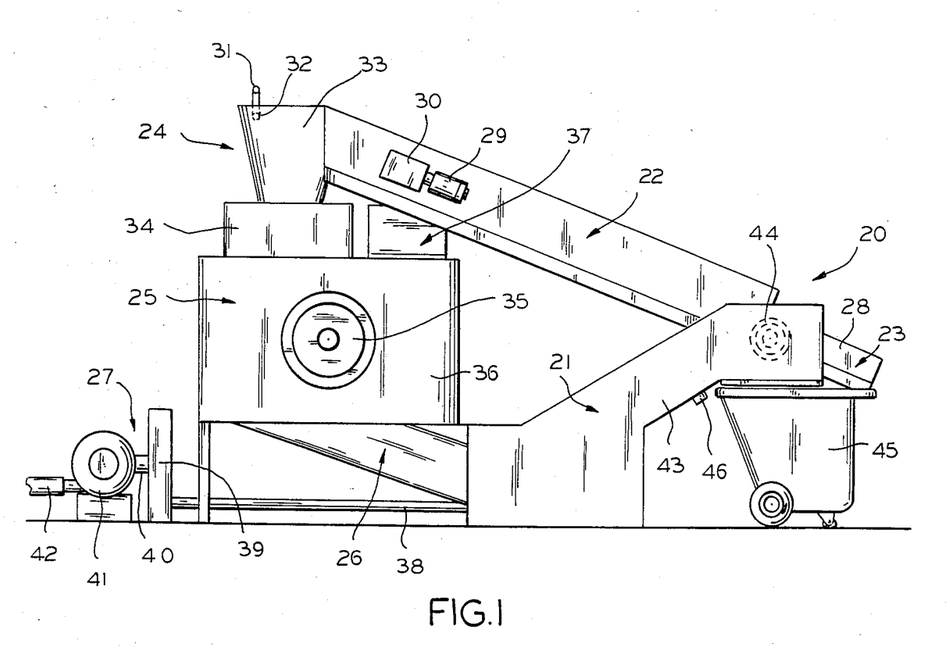
FIG. 1 of the drawings is an elevated side schematic view of the present waste disposal system showing, particularly, its system input means, waste delivery means, preliminary processing means, rotary hammermill assembly, liquid solid particle separation means, and system vacuum ventilation means.

Applicants' waste disposal system 20 is shown in FIG. 1 as comprising waste delivery means conveyor 22 having system input region 23 with side structure 28. As shown in FIG. 1, the waste delivery means conveyor apparatus is operably run by motor 29 connected to transmission mechanism 30 for bringing the waste articles up to and into chute 33 (FIG. 2) operably attached to preliminary waste processing housing 34 in preliminary processing means 24. After the waste articles are processed into relatively smaller waste article fragments within preliminary waste processing means 24, they are conveyed into hammermill 25 within hammermill housing 36 for subsequent disintegration into relatively fine waste particles.

The disinfectant impregnated waste particles are then transferred to hammermill transmission means 26 to solid particle-liquid separation means 21 including separator housing 43 and conveyor sieve motor means 44, for subsequent disposal of separated liquid by liquid evacuation means (not shown in FIG. 1) and independent solid waste evacuation means 45 positioned proximate to solid waste evacuator sensor 46 beneath solid liquid separator 21.

Also shown in FIG. 1 are vacuum ventilation extension conduit 38 leading to filter 39, conduit 40 between filter 39 and exhaust fan 41 and ventilation exhaust means 42 through which filtered ventilated air is discharged from ventilation exhaust system 27 into the atmosphere. Switching control system 37, in co-operation with a computer, sequences and controls the switching operations of the various motor driven components as well as sequences and controls all liquid and lubricant processes.

Figure 2:
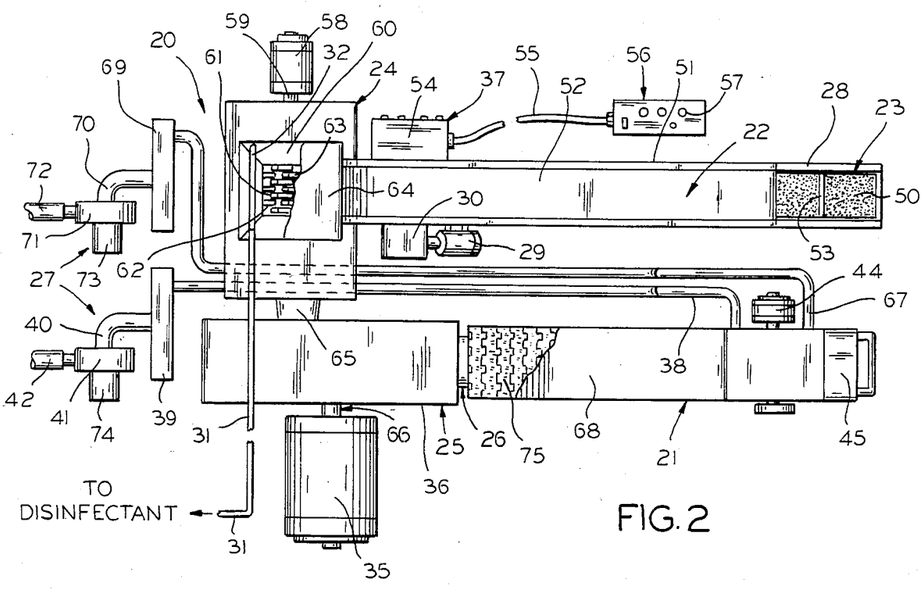
FIG. 2 is a top plan schematic view of the waste disposal system of FIG. 1 showing the same operational components thereof together with its switching system component means, disinfectant spray applicator and additional structure of the vacuum ventilation means.

Waste disposal system 20 is also shown in FIG. 2 which displays, in increased detail, system input means 23 in which the lowermost end of waste delivery conveyor apparatus 50 is shown together with lateral bar 53 for assisting in the delivery of waste articles from the first delivery end to the second delivery end, with said first delivery end proximate to the system input wall structure 28. Waste articles continue being conveyed upwardly within waste delivery means housing 51 having housing cover 52, from which the one or more draped split curtains (not shown in FIG. 2) are suspended. Motor 29 coupled to conveyor transmission 30 operates, through rotation, conveyor apparatus 50 so as to deliver the waste articles into the preliminary processing means 24.

Disinfectant conduit 31 is also shown in FIG. 2 for transmitting disinfectant from the disinfectant storage means to disinfectant liquid spray means 32 operably positioned over preliminary waste processing chute 60 underneath chute cover 64. Below chute 60 positioned within housing 34 of preliminary waste processing means 24, is a dual element shredder having rotating elements 63 and 61 together with stationary members such as member 62 spaced between the toothed disks thereof, for preliminarily shredding and cutting the waste articles introduced therewithin. The preliminary waste processing means is driven by motor 58 operably connected by shredder axle 59 to both elements 61 and 63 within the shredder.

Fragmented waste articles combined with the impregnating disinfectant liquid solution introduced by spray means 32 is then reintroduced through fragment-solution conduit 65 leading into hammermill 25 at a position offset from the center of the hammermill itself. Hammermill motor 35 transmits rotary movement through coupling 66 to the primary rotating member and hammers of hammermill 25 (not shown in FIG. 2) located within hammermill housing 36 to disintegrate the waste fragments and liquid solution into a particle-liquid solution which is transferred via hammermill transmission means 26 into liquid-solid separator 21. Conveyor sieve 75 located underneath liquid solid separator housing cover 68 serves to separate solid waste particles from the disinfectant liquid within liquid-solid separator 21, enabling the release of primarily liquid disinfectant to appropriate sewerage drain lines as well as enabling evacuation of solid particulate into solid waste evacuation means 45. The conveyor sieve 75 is operated by motor 44 located at the top of liquid solid separator 21. FIG. 2 additionally illustrates the connection of ventilation extension conduits 38 and 67 which are operably and independently connected to filters 39 and 69 and exhaust fans 41–74 and 71–73, respectively, comprising the vacuum ventilation system 27 so as to enable exhaust of prefiltered ventilated air through exhuast conduits 42 and 72, respectively.

Also shown in FIG. 2 are system control switch means 37 within housing 54 as well as remote conduit 55 connecting remote test switching apparatus 56 which enables test switching of the various operational components of the waste disposal system by enabling a single operator to remotely test an isolated structural component, while permitting simultaneous viewing of the results of such component testing through utilization of remote switches such as remote switch 57.

Figure 3:
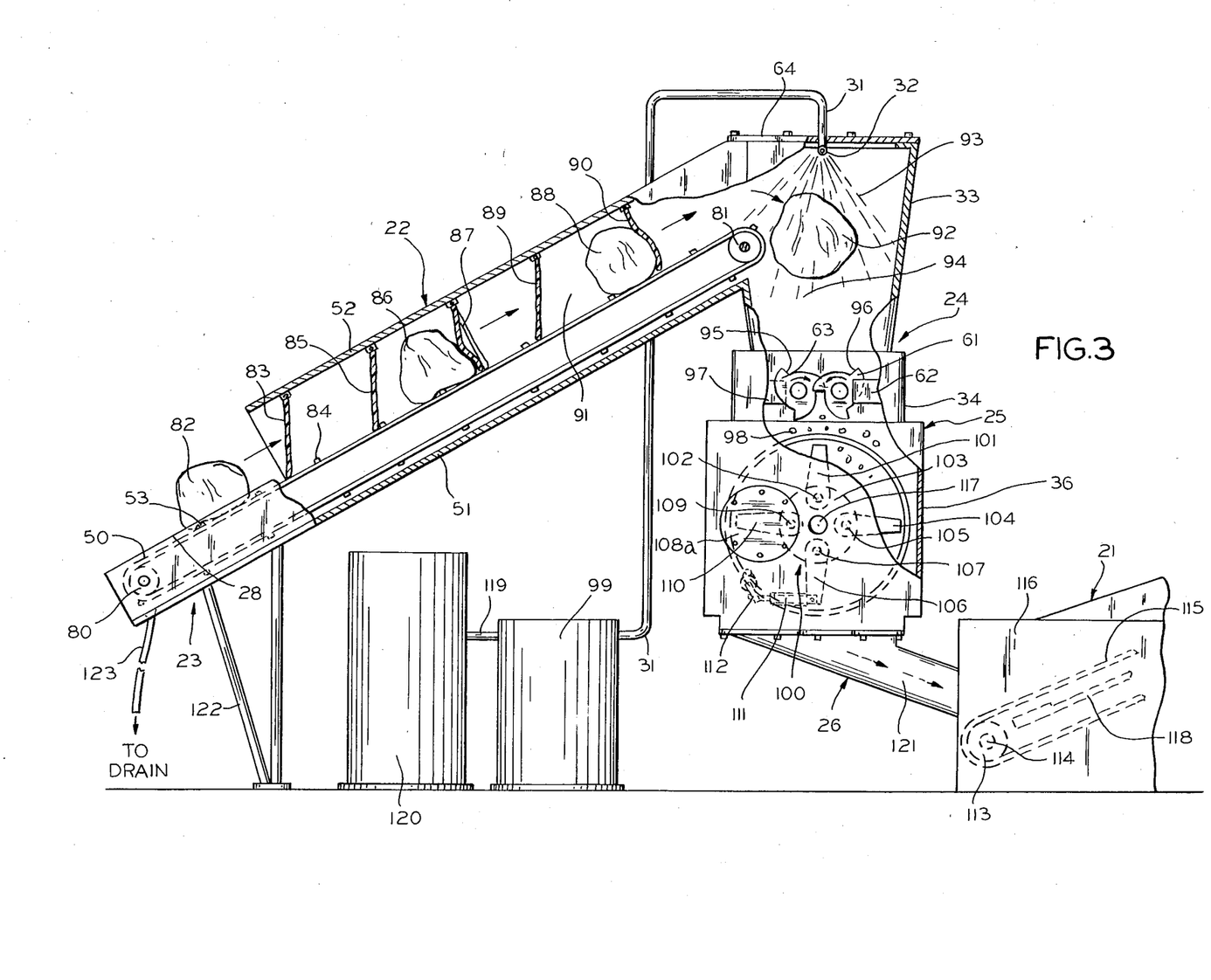
FIG. 3 is an elevated side view, in partial cross section, showing the system input and waste delivery means delivering contaminated waste articles to the delivery chute positioned immediately above the preliminary processing shredder, as well as a portion of the rotary hammermill means and solid particle-liquid solution separator means, which have been illustrated in an orientation of attachment opposite to that of actual configuration, solely for purpose of illustration, as well as showing the system's disinfectant storage and disinfectant generation means.

Waste delivery means 22 is additionally shown in FIG. 3 together with system entry side member 28 proximate to the system input means 23. Accumulated waste articles 82, 86, 88 and 92 are shown being processed through the waste disposal 20 with waste articles 82 being inserted at system input 23 into said system atop elastomeric conveyor belt 50 with lateral bar 53 towards prompting secure movement of the waste articles off the inclined structure of waste delivery means 22. Waste delivery means 22 further includes conveyor pulleys 80 and 81 in which 81 is operably connected to motor means 29 and transmission means 30 from FIG. 2, for operation of conveyor belt 50, as well as waste delivery support structure 122 and waste delivery apparatus housing portions 51 and 52. As accumulated waste articles progress upwardly within chute 91 formed by conveyor housing 51, the articles pass a series of split vinyl curtains such as curtains 83, 85, 87, 89 and 90, all suspended from housing cover 52 and interposed for the purpose of collectively obstructing an inadvertent backflow of potentially contaminated air and particles from further disposal operations "downstream" of the waste delivery means, and for reducing noise. These slitted curtains further permit uninterrupted passage of the accumulated waste articles on the conveyor belt while still permitting the entry of air into the system proximate to the system input means for appropriate ventilation in one direction, namely into and through the overall disposal treatment process prior to release from the exhaust and filter means. Also shown embodying waste delivery means 22 are lateral bar 84 between split curtains 83 and 85 as well as drain assembly 123 positioned in the lowermost portion of system input means 23 to enable the rinsing down of waste delivery means 22 between disposal treatment operations, as desired, towards rinsing away potential waste particles which may be present on conveyor belt 50 as well as rinsing down any accumulations of disinfectant spray which may have misted or migrated back into the waste delivery area.

Disinfectant spray means 31 is shown attached to spray bar 32 at the top of chute 33 which is operably attached to conveyor housing 51 in sealed configuration. Spray bar 32 is preferrably located immediately below preliminary processing means chute cover 64 and is operably connected to disinfectant conduit 31 emanating immediately from disinfectant spray storage means 99 which, in the preferred embodiment, is further connected by disinfectant conduit means 119 to disinfectant generation means 120. Spray bar 32 or a similarly situated spray mechanism above the shredder, may also be used during extended shut downs in system operation to channel firstly diluted disinfectant, then water, and finally a water-soluble oil and water over the exposed machine parts to fight corrosion of these parts from the disinfectant solution used during waste treatment. A protective film of oil is thus directed to such machine parts, coating them until system startup.

In FIG. 3 accumulated waste articles 92 are shown falling by gravity off of waste delivery means conveyor belt 50 into chute region 94 while it is being sprayed with disinfectant spray liquid 93, preferably at a rate approximating thirty gallons per minute. As previously discussed, in the preferred embodiment, the disinfectant spray itself comprises a two tenths (0.2%) percent concentrated solution of sodiumhypochlorite (NaOCl) having a pH of 8.5 which is generated on an "on-site basis" through electrolytic action on an appropriate brine solution. Alternatively, an ozone disinfectant may be utilized.

Waste articles 92 in their unprocessed form continue to be sprayed continuously as same fall into the nip formed between counter-rotating shredder elements 63 and 61 within shredder assembly housing 34. Shredder element 63 utilizes, preferably, a plurality of shredded teeth such as tooth 95 while shredder 61 relies upon a plurality of teeth, preferably three in number, as exemplified by shredder tooth 96, and both of the dual elements 61 and 63 respectively co-operate with jogging members 62 and 97 respectively, which are fixed in stationary position between adjacent positions along the cutting disks. Additionally, preliminary processing housing 34 is shown directly communicating in sealed attachment with chute housing 33 so as to effectively integrate preliminary processing means 24 into the substantially sealed uni-directional ventilation vacuum system.

The waste articles such as those disclosed by waste articles 92 are pre-shredded and cut into substantially smaller fragments 98 which, in turn, are routed into an offset entry aperture adjacent fragment solution channeling means (not shown in FIG. 3), attached to hammermill 25 at a position in hammermill housing 36. Fragments 98 accordingly enter the hammermill at a substantially offset position relative to hammermill axle 117 and are further disintegrated through the violent hammermill driving action of primary rotating member 103 with hammer members 101, 104, 106 and 110, operably and pivotally attached at rotating pivots 102, 105, 107 and 109, respectively. The entire hammermill chamber 100 comprises a substantially thin laterally position cylindrical cavity which is also shown in FIGS. 6, 7, 9 and 10 together with hammermill housing 36 operably and sealingly attached to preliminary processing means housing 34. Additionally shown in phantom in FIG. 3 are covering door 112 and door positioning means 111, preferably comprising a pneumatic piston responsive to a jam sensor for opening the overload release aperture for expedited release of accumulated particles-liquid solution processed within hammermill chamber 100.

Hammermill transmission means 26 is shown disposed in opposite direction solely for purpose of illustration in FIG. 3 and is operably sealed to the bottom of hammermill housing 36 for the purpose of routing disintegrated solid particle-disinfectant solution from the hammermill for further processing by the solid waste-liquid solution separator means 21, shown in FIG. 3 as including solid-liquid separator housing 116 operably sealed to the second end of waste particle-liquid solution transmission means 121 as well as including conveyor sieve 115, routing plate 118 and lower separator pulley 113 with pulley axle 114.

Figures 4, 5:
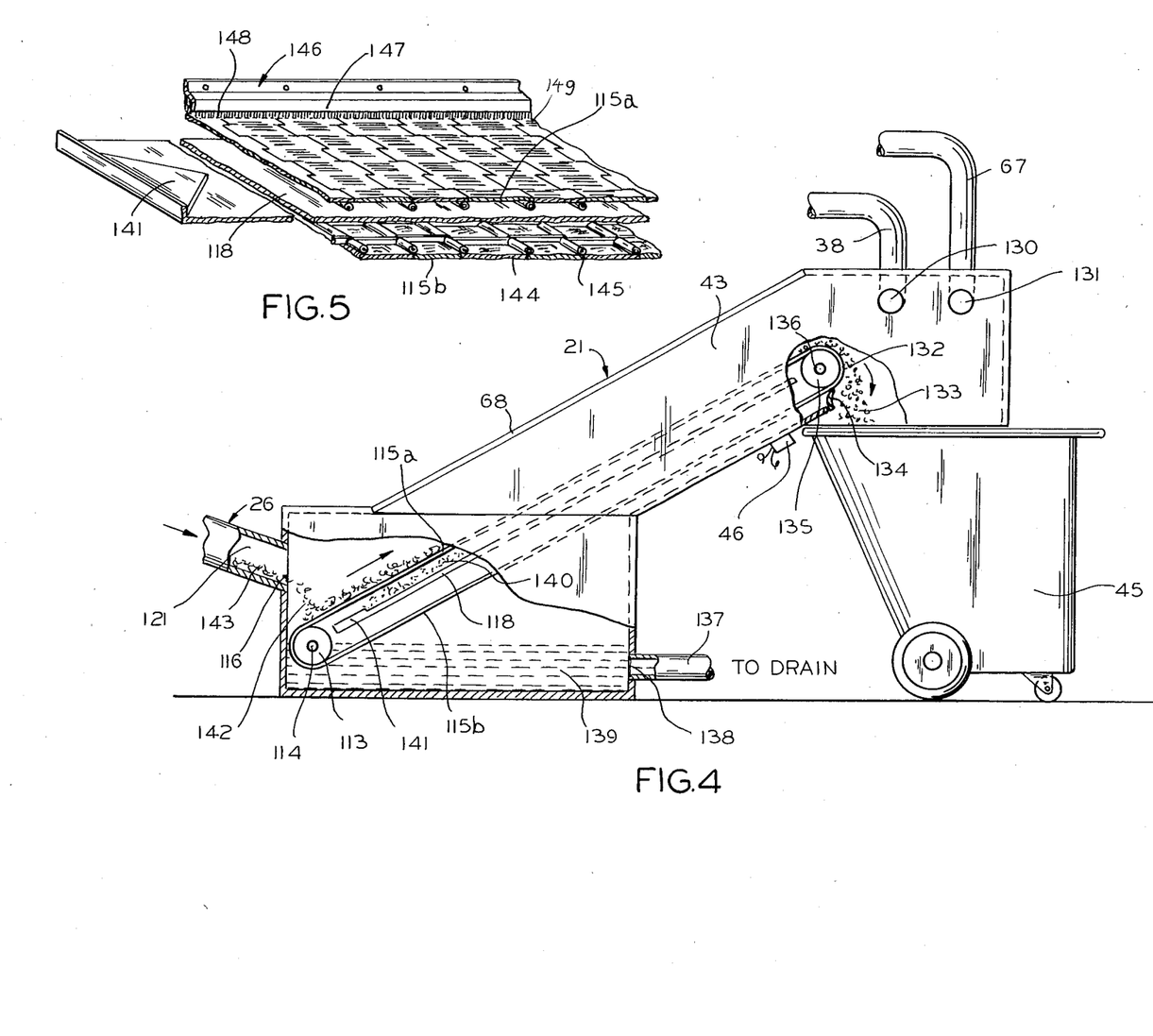
FIG. 4 is an elevated side view, in partial phantom, showing the waste particle-disinfectant liquid separation means and particularly showing entry of liquid impregnated particulate waste thereinto as well as the operational structure for separating such solid waste from such liquid waste together with liquid and solid evacuation means and vacuum ventilation connections.
FIG. 5 is a top perspective view of the continuous conveyor sieve located within the solid-liquid separation means of FIG. 4 showing particularly, the structure of the articulated belt segments, the shoulder rail brush assembly adjacent the edges of the conveyor sieve as well as the plate member operably interposed between the top portion of the conveyor and the bottom returning portion of the conveyor, to preclude the dropping of solid particulate onto the underside of the returning bottom conveyor sieve portion.

Liquid-solid separator 21 is shown in FIG. 4, in partial section, with hammermill transmission means 26 forming a chute 121 in which a combined solution of fine particulate of solid waste and liquid disinfectant enters the entry aperture region 116 of the liquid-solid particle separation means 21. Immediately below entry aperture 116, the combined solid-liquid solution falls onto conveyor sieve portion 115a, which portion is the top continuously rotating portion of sieve conveyor 115 with sieve portion 115b being the bottom returning portion of said continuous looped belt apparatus. At this point the combined mixture is moved upwardly through pulleys 113 and 135, with pulley axles 114 and 136 respectively, with the majority of excess disinfectant liquid solution being separated from the particulate waste supported on conveyor sieve 115a through gravity, said excess disinfectant liquid being permitted to fall through a substantial plurality of small release slots within the component elements of conveyor sieve 115a. The remaining disinfectant impregnated solid particles 132 proceed towards pulley 135 where they either fall off as solid particles 133, into solid waste evacuation means 45 or are alternatively scraped off conveyor sieve 115 through scraper 134 spanning the lateral width of conveyor sieve 115a, likewise into solid waste evacuation means 45. If waste evacuation means 45, here comprising a wheeled cart, is not in operative position under pulley 135 and belt end 115a to receive the solid waste, such absences being detected by position electric-eye sensor 46, this in turn shuts down the operation of liquid-solid waste separation means 21. While solid waste is being delivered to solid waste evacuation means 45, liquid disinfectant falling from the conveyor sieve belt accumulates in bottom 139 of the lower housing of separation means 21, accumulating at bottom region 139 for release through drain 137 to, for example, municipal sewerage lines.

Also shown in FIG. 4 is routing plate 141 positioned between upper conveyor sieve portion 115a and lower conveyor sieve portion 115b for the purpose of routing falling disinfectant liquid and any small amount of relatively fine solid particles which may pass through conveyor sieve 115, such as liquid solution fine particulate 140, about the back of the bottom side of lower conveyor sieve 115b, so as to avoid potential problems with the undesirable distribution of solution and particulate along the backside of the conveyor sieve to preclude inadvertent jamming or wear problems. Router 141 in routing plate 140 distributes this primarily liquid solution beyond the periphery of the lower belt portion 115b so as to accumulate same in the lower resevoir region 139 of the liquid solid separator housing 43 which, again, is operably and sealingly attached to hammermill transmission 26, and which further includes housing cover 68 which, preferably, is removable for facilitated access into the liquid-solid separation means. Through such a construction, liquid-solid particles 143 entering from transmission means 26 are introduced onto the conveyor sieve at 142 for subsequent separation into disposable liquid 139 and disposable solid waste 132 and 133.

Also shown in FIG. 4 are ventilation extension attachment regions 130 and 131 operably attached to ventilation circuit extensions 38 and 67 respectively. Each of these two independent ventilation circuit extensions are affixed at the farthest end of the solid-liquid particle separation means 21 for channeling the air from same to separate and independent filter and exhaust fan components while maintaining the air ventilating through the overall disposal system 20 in a safe, controlled uni-directional route.

A portion of conveyor sieve 115 is shown in FIG. 5 in which upper sieve portion 115a and lower sieve portion 115b are shown together with routing plate 118 operably interposed therebetween and extending the width at least equal to the width of the conveyor sieve itself, so as to be able to distribute falling liquid and fine particulate away from the backside components 144 and 145 of lower sieve portion 115b. Router 141 is shown which reroutes the falling primarily liquid solution about the edges of the lower sieve portion 115b as same is routed by gravity towards router 141. Additionally shown in FIG. 5 are conveyor sieve shoulder region 146 with shoulder member 147 and brush element 148 positioned adjacent to the longitudinal edge of conveyor sieve 115 to further route the separated solid waste particles toward the solid waste particle evacuation means. The conveyor sieve is shown to be a conveyor belt made up of separator belt components such as belt component 144 which is possessed of a plurality of slotted apertures such as aperture 149, of a size capable of releasing the majority of disinfectant liquid solution mixed with the solid waste particles introduced onto sieve portion 115a, while being incapable in size of releasing any substantial volumes of solid waste particles deposited thereon so as to substantially direct most of the solid waste particles directly to the solid waste particle evacuation means.

Figure 6:
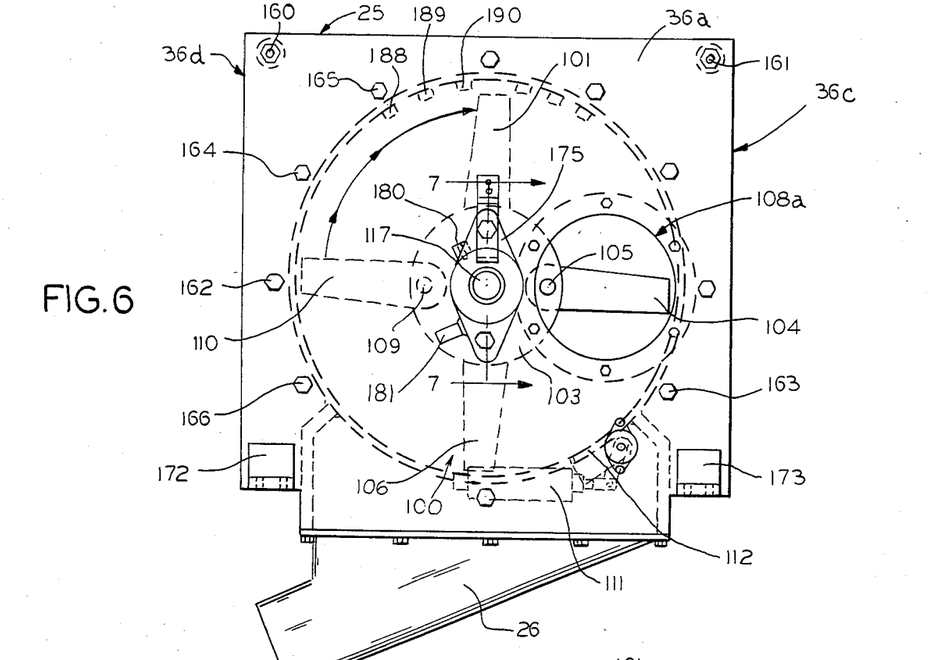
FIG. 6 is an elevated side view of the rotary hammermill apparatus particularly displaying the hammermill housing, the hammer elements, the primary rotating element, together with the hammermill transmission chute and jam release door.
Figure 7:
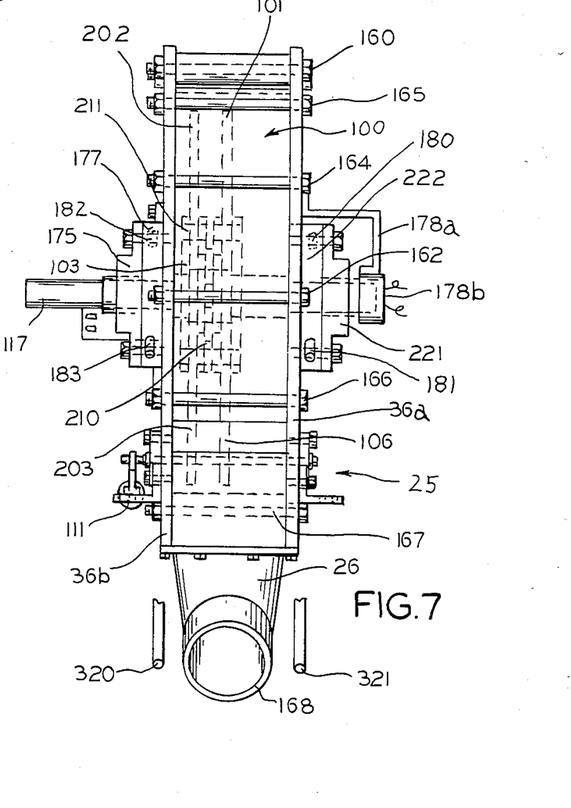
FIG. 7 of the drawings is an elevated front view of the hammermill apparatus of FIG. 6 showing particularly the positioning of the primary rotating element and hammers within the hammermill housing, the hammermill bearing and bearing spacer construction as well as the sensing detector and flushing conduits associated therewith.

Hammermill 25 is shown in FIG. 6 with housing 36a through 36d in operable and sealed attachment to the second end of the fragment solution channeling means emanating from preliminary waste processing housing 34. This operable and sealed connection occurs at entry aperture 108a in housing panel 36a. The various housing components are operably sealed to one another through a bolt-spacer arrangement so as to form interior hammermill chamber 100, through bolts such as bolt 160 through 166 and spacer section 167 (as shown in FIG. 7). Fragment jogging members such as jogging members 188 through 190 are positioned in the upper interior periphery of the hammermill housing chamber 100 for cooperation with pivotally rotatable hammers 101, 104, 106 and 110. Hammers 104 and 110, for example, are pivotally attached to primary driving element 103 at pivots 105 and 109, respectively. Also shown in FIG. 6 are bearing assembly 175, incoming and outgoing flush attachment fittings 180 and 181, which co-operate with a bearing spacer assembly located directly behind hammermill bearing assembly 175 towards improving avoidance of contamination and/or excess friction created from the potential migration of waste particle disinfectant solution along hammermill axle 117. Attached to these respective inlet and outlet fittings 180–181, preferably located on each side of the hammermill so as to accommodate each said hammermill bearing assembly, are incoming and outgoing flushing conduits such as outgoing flushing conduits 320 and 321 shown schematically in FIG. 7. These conduits enable the introduction of flushing medium through the bearing spacer to, in turn, clean out these portions of migrating waste particles and disinfectant solution for transmission of then-contaminated flush medium to liquid solid particle separation means 21. Also shown in FIG. 6 are hammermill transmission means 26 affixedly sealed to hammermill housing assembly 36a through c, emergency aperture cover door 112 with pneumatic door positioning means 111 and mounting regions 172 and 173 through which the overall hammermill apparatus is mounted to its supporting structures.

The hammermill assembly of FIG. 6 is also shown in FIG. 7 in which rotary hammermill means 25 includes housing faces 36a and 36b, hammers 101, 106, 203 and 202, with hammers 101 and 202 attached at pivot pin 211 and hammers 106 and 203 attached at pivot pin 210. Also shown in FIG. 7 are hammermill transmission means 26 with second end 168, and flushing conduits 320 and 321. Primary rotating element 103 is shown attached to hammermill axle 117, with said axle being supported by bearing assemblies 175 and 221, respectively, each spaced away from the housing by bearing spacers 177 and 222, respectively. Flushing fittings 180 and 181 on bearing spacer 222, and fittings 182 and 183 on bearing spacer 177, respectively co-operate to appropriately flush potentially migrating waste and disinfectant from entering the respective outwardly positioned bearing assemblies 221 and 175. Chamber 100 is formed through compressive attachment of housing sides such as housing components 36a and 36b, through bolt and spacer devices such as bolts 160, 165, 164, 162, 166 and spacer 167. Torque indicating sensor 178b is also shown positioned about a portion of hammermill axle 117 in order to detect drastic slowdowns in the rotary torque of same, in order to actuate covering door operator 111 towards rapid evacuation of particle-liquid solution from within hammermill chamber 100; with sensor 178b maintained in position about axle 117 through sensor bracket 178a.

Figure 8:
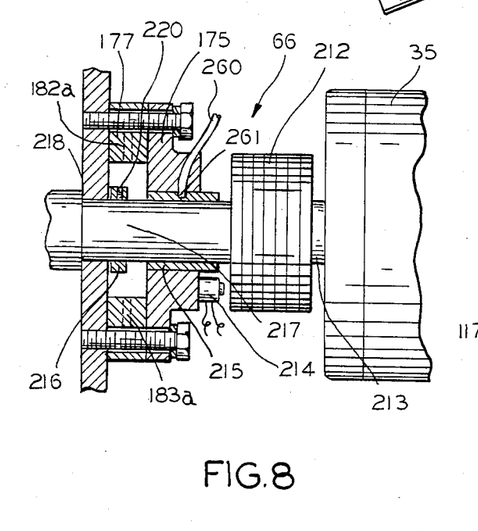
FIG. 8 is an elevated side view of a portion of the rotary hammermill means showing, particularly, the hammermill motor and breakaway coupling component, the bearing assembly showing utilization of a bearing spacer for continuous flushing during operation of the hammermill, the slinging component to assist in such flushing, and a constant greasing fitting to constantly lubricate the bearing elements.

Coupling means 66 is shown in FIG. 8 as comprising a quick release coupling apparatus 212 which is capable of automatically releasing motor means 35 from its connection along motor axle 213 from primary rotating member 103, upon the occurrence of a torque limiting jam. Upon separation of motor 35 a portion of quick release coupling 212 moves leftwardly to contact sensor switch 214 which serves as a warning device for notifying the operator of the occurrence of the motor disconnection. Electrical control means operably connected between coupling 212 and motor 35 assist in automatically winding down the operation of the motor so that it cannot freely accelerate with no load. A closer view of one bearing contamination protection means is also shown in FIG. 8 in which bearing assembly 175 is spaced apart from hammermill housing portion 218 by bearing spacer 177 having flush entry means 182a and flush exit means 183a operably associated therewith. Through such an arrangement, flushing medium can enter the center of the bearing spacer and, through centrifugal agitation of slinger 216 fastened to hammermill axle 217 at fastening means 220, such flushing medium is pumped into, through and out of said bearing spacer 177, carrying with it potential waste particles and disinfectant solution which may migrate towards the bearing elements 215 of bearing 175 along axle 217. As an additional means for prevention of contamination, grease conduit 260 is provided for connection with a pressurized greasing apparatus at bearing region 261, for intermittently and effectively circulating fresh greasing medium into and about bearing elements 215 to further preclude the undesired contamination, corrosion and/or undesired creation of excess friction about these bearing elements while further flushing out any additional traces of migrating waste particles and disinfecting solution which may reach these rotating elements, notwithstanding the flushing operation occurring within bearing spacer 177.

Figures 9, 10, 11, 12, 13:
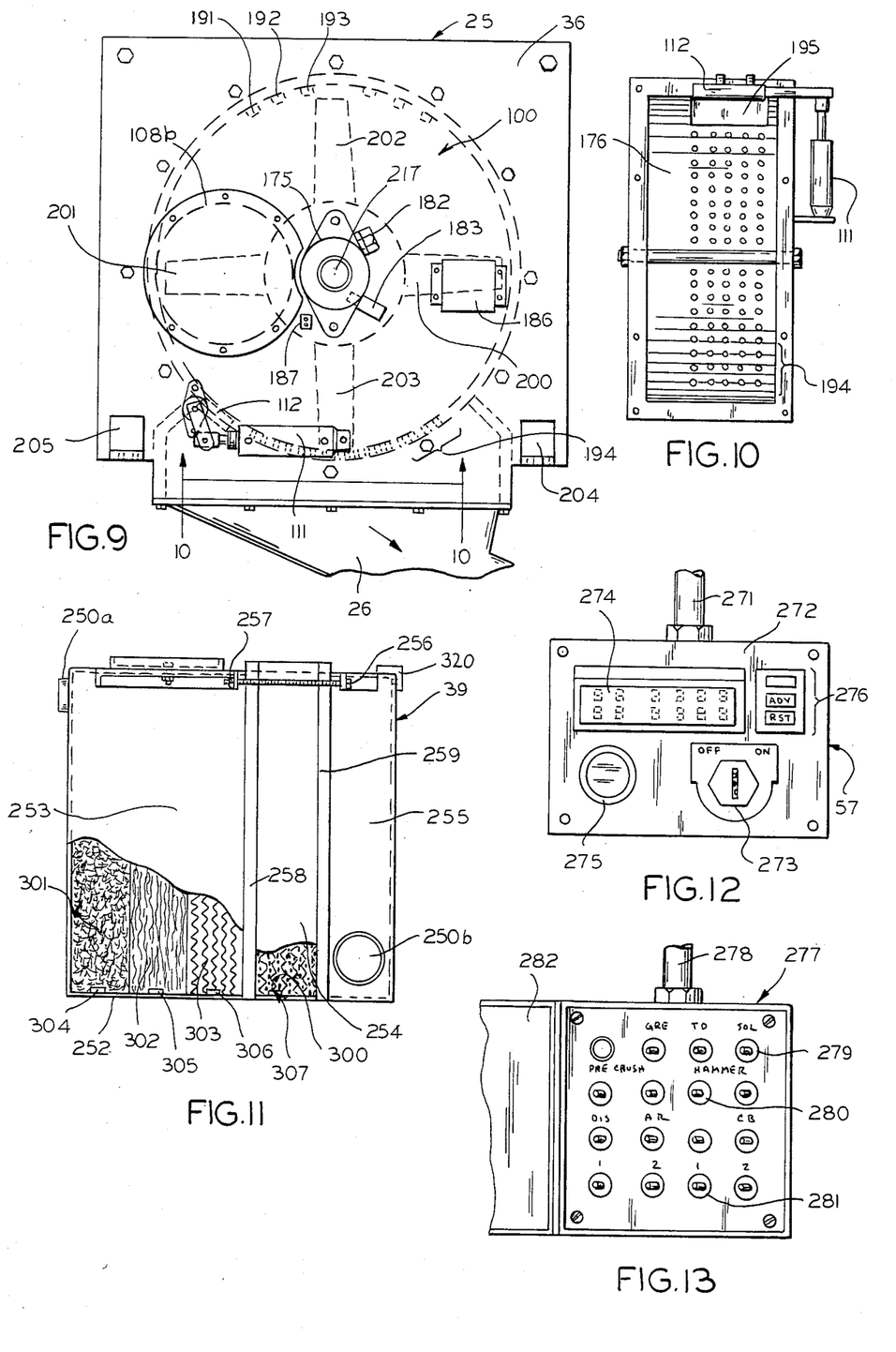
FIG. 9 is an elevated side view of the hammermill apparatus of FIG. 6 taken from the opposite side showing, particularly, fabrication and placement of the release apertures, the jam release door and activation mechanism therefor, the jogging elements at the top of the hammermill housing and bearing assemblies for rotation of the primary rotating element.
FIG. 10 is a bottom plan view taken along lines 10—10 of FIG. 9 and looking in the direction of the arrows showing, particularly, the orientation of the release apertures and jam release door assembly with the associated activation mechanism for opening same upon occurrence of a jam.
FIG. 11 is a side elevational view of the preferred embodiment of filter assembly showing, in partial breakaway fashion, the four different filter media utilized within same prior to discharge of the ventilated air from out of the disposal system.
FIG. 12 is a front elevational view of the switching control means particularly showing the diagnostic indicia in place thereupon.
FIG. 13 is a front elevational view of the system switching control means comprising a remote test switching apparatus for single-handed testing of component functions along the waste disposal system.

Hammermill 25 is also shown in FIG. 9 together with housing 36, hammermill chamber 100, jogging members 191 through 193, hammers 200 through 203, hammermill axle 217, flushing fittings 182 and 183, bearing assembly 175, sealed access port 108b, disconnection sensor bracket 187 as well as electrical switching conduit box 186, for enclosure of sensor circuitry, and mounting means 204 and 205. Cover door 112 is shown connected to positioning means 111 capable of opening and exposing emergency release aperture 195 (FIG. 10) in the event of a jamming situation. Additionally, shown in FIG. 9 are a series of normally operative release apertures such as release apertures 194 which, in the preferred embodiment, comprise a series of columns and rows of half inch diameter release apertures through which the disintegrated solid waste particles, together with impregnated disinfectant solution may be released for exit through hammermill transmission means 26. Apertures 194 and jam release aperture 195 is also shown in the bottom plan view of FIG. 10 in which cover door 112 is in its open position with positioning means 111, a pneumatic piston extended to open same upon the occurrence of such a jam, to release solid and liquid solution from the bottom circular portion 176 of hammermill housing 36.

As described hereinabove the system vacuum ventilation means includes two or more independent ventilation circuit extensions in sealed affixation to the solid-liquid particle separator for channeling air, in a single controlled direction, through the ventilation circuit. Filtering means are operably associated with each of the two independent ventilation circuit extension means to filter mists, vapors, waste particles and bacteria from the air before releasing the air from the system. In FIG. 11 one such filter 39 is shown as comprising a series of filter subhousings 253 through 255 with a particular stainless steel hepa housing delineated at removable sections 258 and 259 for cooperation with hepa filter 307 within hepa filter housing 254. Access to the hepa filter is accomplished through disassembly of hepa housing fittings 256 and 257. Air impregnated with said mists, vapors and/or particulate are introduced at filter entry 250a to firstly pass through hog hair filter 301, is then passed through polyester filter 302 and pleated filter 303 before being passed through hepa filter 307. Saturation of the filters is detected by vacuum sensing switch 320 capable of signalling the operator at such time that air pressure within chamber 255 is affected by a saturated filter. The well-filtered air exits from the filter for discharge through filter exit 250b and subsequent exhaust fans such as exhaust fans 41 and 74 of FIG. 2. Hog hair filter 301 serves to remove mists and saturated vapors from the ventilated air while polyester filter 302 serves to stop particles, together with high surface coverage pleated filter 303. The stainless steel interior of hepa filter housing 254 is preferably covered, together with aluminum separators 300 within hepa filter 307, with an epoxy substance to prevent corrosion by any remaining chlorine vapors which may still be present in the air as it travels through hepa filter 307 in hepa filter housing 254.

General switching control 57 is shown in FIG. 12 as including a general on/off switch 273 with indicator light 275 and diagnostic means 274 and 276 within switch housing 272, which electrical components are operably and electrically connected through conduit 271 to the power supply and controlling computer which sequences the operation of the various components embodied by the waste disposal system. The system switching control means further comprises remote test switching apparatus 277 operably connected to the sequencing and controlling computer through electrical conduit 278 which includes independent switching means, such as switching means 279 through 281 for each of the motorized and fluid operated components within housing 282, so that a single individual can test, in isolation, any one of the structural operable components of the waste disposal system while being capable of simultaneously viewing the operation of each said component without having to run back and forth to the general switching means of FIG. 12, and without the need for a second operator.

As mentioned hereinabove relative to the hammermill, other components of the waste disposal system such as the waste delivery means, the preliminary waste processing means, the liquid solid particle separation means, the system vaccum ventilation means and the system switching control means are contemplated as being mounted on elastomeric mounting means to further isolate and effectively reduce the extent of vibration and noise emanating from these particular components.

The foregoing description and drawings merely explain and illustrate the invention and the invention is not limited thereto except insofar as the amended claims are so limited as those skilled in the art who have the disclosure before them will be able to make modifications and variations therein without departing from the scope of the invention.

What is claimed is:

1. A waste disposal system for treating and disposing of infectious waste articles in a substantially controlled closed aseptic environment and for converting said infectious waste articles into a safely disposable noninfectious and nontoxic residue through the thorough disintegration and disinfection of such articles, said system comprising:

system input means into which accumulated quantities of said waste articles are initially placed for subsequent treatment and disposal of same;

waste delivery means operably connected to said waste input means at a first delivery end for transferring said accumulated quantities of said waste articles to a second delivery end, said second delivery end being positioned substantially opposite said first delivery end;

preliminary waste processing means operably positioned proximate to the second delivery end of said waste delivery means for preliminarily restructuring said waste articles into substantially small waste fragments for further treatment and disposal of same by said waste disposal system;

disinfectant spray means operably positioned adjacent one or more of said second delivery end of said waste delivery means and said preliminary waste processing means for enveloping and impregnating one or more of said waste articles and said waste fragments in a bacteria killing disinfecting liquid solution through the spray emitted by said spray means and the operation of said preliminary waste processing means;

said disinfecting liquid solution and waste fragments being jointly directed from said preliminary waste processing means by fragment-solution channeling means having a first and second end with said first end being operably positioned adjacent said preliminary waste processing means, rotary hammermill means operably attached to the second end of said fragment-solution channeling means for receiving said waste fragment-disinfectant solution from said fragment solution channeling means, and for violently disintegrating same at a substantially high speed, into a waste particle-disinfectant solution, said rotary hammermill means being powered by hammermill motor means operably coupled thereto;

hammermill solution transmission means having a first and second end through which said waste particle-disinfectant solution is routed out of said rotary hammermill for further treatment and disposal by said waste disposal system;

liquid-solid particle separation means operably attached to the second end of said hammermill transmission means for separating, on a continuous basis, said disintegrated particles of solid waste from said enveloping and impregnating disinfectant liquid;

said liquid-solid particle separation means including operable connections to liquid evacuation means and solid particle evacuation means for disposal of said disinfectant liquid and said solid waste particles respectively;

system vacuum ventilation means operably associated with said disposal system for effectively precluding the inadvertent release of bacteria and other contamination during the treatment and disposal of said waste articles by said system; and system switching control means operably associated with one or more of said waste input means, waste delivery means, preliminary waste processing means, disinfectant spray means, rotary hammermill means, liquid-solid particle separation means and system vacuum ventilation means for controlling the activation and sequencing of one or more of same relative to one or more of the others.

2. The waste disposal system of claim 1 in which the invention further comprises disinfectant storage means for containing accumulated quantities of said disinfectant liquid, said disinfectant storage means being operably connected to said disinfectant spray means for supplying, through disinfectant conduit means, desired amounts of disinfectant liquid for spraying of same onto said waste articles at said position adjacent one or more said second delivery end of said waste delivery means and said preliminary waste processing means.

3. The waste disposal system according to claim 2 in which the invention further comprises disinfectant generation means;
  said disinfectant liquid comprising a disinfectant solution of sodiumhypochlorite and water;
  said disinfectant generation means comprising an on-site disinfectant generator operably coupled to said disinfectant storage means for creating said sodiumhypochlorite compound through electrolytic treatment of a brine solution,
  said generated sodium hypochlorite being combined with water after storage in said disinfectant storage means to form a two tenths (0.2%) percent concentrate solution having a pH of 8.5;
  said generated disinfectant, upon combination with said water to form said two tenths (0.2%) percent concentrate solution, being supplied to said spraying means through said disinfectant conduit means.

4. The invention according to claim 1 in which said waste delivery means comprises a substantially inclined motorized conveyor apparatus;
  said conveyor apparatus including, at a first end, said system input means for initial placement of said quantities of said waste articles for subsequent treatment and disposal,
  said conveyor apparatus further including a substantially flat continuous conveyor belt with laterally positioned bars positioned thereupon for effectively transferring said waste articles to said second delivery end proximate the preliminary waste processing means, as a driving motor operably attached thereto said conveyor apparatus is activated by said system switching control means to transfer said waste articles thereupon.

5. The invention according to claim 4 in which said laterally positioned bars and said conveyor apparatus belt are formed of a substantially elastomeric material,
  said elastomeric material being selected from the class of elastomeric materials composed of urethane and rubber.

6. The invention according to claim 4 in which said conveyor apparatus includes one or more draped slitted curtains suspended immediately above said conveyor belt along the longitudinal path of said conveyor belt;
  said slitted curtains permitting uninterrupted passage of said accumulated waste articles thereon said conveyor belt as said conveyor belt moves same from said first delivery end to said second delivery end of said waste delivery means;
  said conveyor apparatus further including a substantially sealed conveyor housing about said conveyor belt,
  said slitted curtains being suspended from the top of said housing and cooperating with said housing to preclude the harboring, backflow and inadvertent release of potential bacteria and backflowing waste particles present in said system at said waste delivery means and for reducing and isolating noise associated with said system.

7. The invention according to claim 6 in which said one or more draped slitted curtains is constructed of a substantially vinyl material to more effectively enable unobstructed passage of said accumulated waste articles on said conveyor belt and to simplify the cleaning of said one or more slitted curtains;
  said conveyor apparatus housing enclosure being constructed of a substantially stainless steel material in the form of a chute to preclude the undesired harboring of bacteria in the proximity of said waste delivery means.

8. The invention according to claim 1 in which said system input means includes, at a position proximate to said first delivery end, drain means located at the lowermost region of said conveyor apparatus to enable the draining of rinsing solution used to rinse said system input means and waste delivery means between operations of said waste disposal system so as to drain away accumulations of disinfectant spray, infected and bacteria laden waste particles.

9. The invention according to claim 1 in which said preliminary waste processing means comprises a dual element counter-rotating cutter-shredder apparatus,
  each of said dual elements possessing a plurality of three tooth shredding disks which are respectively and sequentially articulated in alternating fashion between one another,
  each of said cutting disks of said dual elements cooperating with a series of stationery jogging members operably disposed in sequential fashion within adjacent positions amongst said cutting disks,
  said cutter-shredder being powered and driven by cutter-shredder motor means operably attached to each of said counter-rotating dual elements.

10. The invention according to claim 9 in which said preliminary waste processing motor means includes a torque reactive controlled motor which reacts to overloads occurring within the cutter-shredder means by deactivating and stopping said shredder in the event of jamming therewithin.

11. The invention according to claim 9 in which said preliminary waste processing means is operably disposed in a substantially sealed shredder housing immediately surrounding said dual counter-rotating shredding elements;
  said shredder housing having attached thereto, at its upper region, a substantially sealed chute element in operable communication with a substantially sealed conveyor apparatus housing formed about said waste delivery means,
  said sealed chute element receiving said accumulated waste articles at said second delivery end of said waste delivery means for, in turn, transferring same, through gravity, to the nip formed between said cutting disks among said dual counter-rotating shredder elements in said preliminary waste processing means.

12. The invention according to claim 11 in which said spray means comprises a substantially horizontally positioned spray bar extending the longitudinal length of said dual elements and fixedly restrained thereover, for substantially downward vertical spraying of said disinfectant liquid, from a position along the top of said substantially sealed chute;
  said disinfectant spraying means serving to continuously dispense said liquid disinfectant over said accumulated quantities of waste articles as said articles reach said second delivery end, while said accumulated waste articles fall, by gravity, into said shredder-cutter apparatus for preliminary fragmentation thereof;
  said liquid disinfectant surrounding and impregnating both the waste articles awaiting fragmentation by said shredder-cutter, as well as the fragments being released therefrom into said fragment-solution channeling means, in turn leading to said rotary hammermill means.

13. The invention according to claim 12 in which said sprayer means dispenses said liquid disinfectant spray at a rate approximating thirty gallons per minute onto said waste articles and said waste article fragments therebelow.

14. The invention according to claim 1 in which said rotary hammermill means comprises a high-speed hammermill apparatus capable of violently disintegrating the waste article fragments immersed and impregnated in said disinfectant liquid solution so as to effectively disintegrate said fragments into substantially small waste particles for improved penetration thereby by said disinfectant liquid to, in turn, enable the complete and substantial disinfection of bacteria carried by same,
    said fragment solution channeling means comprising a substantially sealed channel member operably connected in sealed relationship to a sealed preliminary waste processing housing surrounding said preliminary waste processing means, at said first end of said channeling means and in sealed operable connection with a side entry aperture in said rotary hammermill means at the second end of said fragment solution channeling means;
    said rotary hammermill means including a substantially sealed hammermill housing through which said hammermill motor means is operably coupled to the hammermill apparatus disposed therewithin,
    said entry aperture operably positioned in offset fashion within one side wall of said substantially sealed hammermill housing.

15. The invention according to claim 14 in which said hammermill apparatus further comprises;
    a primary rotating member directly and operably connected to said hammermill motor means through hammermill axle means,
    a plurality of hammer members operably mounted for pivotal movement about the outer periphery of said primary rotating member;
    a plurality of fragment jogging members operably positioned at the upper interior periphery of said hammermill apparatus housing for more effectively disintegrating said waste article fragments during rotation of said primary member and hammer members; and
    a plurality of apertures located at and through the bottommost peripheral region of said hammermill housing for release of said waste particle-disinfectant solution after disintegration of same by said rotary hammermill means into the first end of said hammermill transmission means.

16. The invention according to claim 15 in which said release apertures include a plurality of substantially small circular release apertures leading through said hammermill apparatus housing into said first end of said hammermill transmission means; and
    an overload release aperture maintained in a sealed position during normal operation by a releasable covering door operably connected to door positioning means capable of opening said covering door when speed detection means disclose a jamming situation within the hammermill apparatus, thereby expediting the release of accumulated waste particle-disinfectant solution out of said rotary hammermill apparatus and into said hammermill transmission means upon such a jam occurrence,
    said speed detection means comprising a rotary speed sensor positioned about said hammermill axle means for detecting an abrupt reduction in speed thereof to, in turn, activate said covering door to immediately open to more rapidly evacuate waste particle-disinfectant solution from the interior of said hammermill apparatus housing;
    said door positioning means comprising pneumatic piston means operably affixed at one end to said covering door to operate same upon said occurrence of jamming, maintaining same in a closed position at all other times.

17. The invention according to claim 15 in which said primary rotating member of said hammermill apparatus is suspended for rotation about opposite faces of said hammermill housing by a plurality of hammermill bearing assemblies operably communicating with said primary rotating member through said hammermill axle means;
    each of said plurality of hammermill bearing assemblies having means for withstanding contamination from migration of said waste particle-disinfectant solution emanating from within said hammermill housing and along said axle means towards portions of said bearing means, to further preclude corrosion and interference of said migrating particles-solution into said bearing.

18. The invention according to claim 17 in which said means for withstanding contamination in each said bearing assembly comprises;
    a plurality of bearing spacer means each providing a cavity immediately adjacent each said bearing assembly, said bearing spacer in direct and operable communication with respective portions of said axle means;
    an inlet and outlet fitting positioned in each said bearing spacer means permitting attachment thereto of an incoming and outgoing flushing conduit for operable communication with the interior of said bearing spacer means;
    flushing medium pumped through said flushing conduits to enter into and exit from said bearing spacer,
    said flushing medium being pumped continuously during the operation of said hammermill apparatus to flush each said bearing spacer to, in turn, clean out said portions of migrating waste particles and disinfectant solution which could otherwise enter and adversely affect said bearing assemblies.

19. The invention according to claim 18 in which said means for withstanding contamination in each said bearing assembly further comprises a slinger element operably and fixedly attached to said axle means within each said bearing spacer means for further assisting, through the creation of centrifugal dispersion, the flushing of said migrating waste particles and disinfectant solution out of said bearing spacer and through and out said exiting flushing conduit.

20. The invention according to claim 17 in which said means for withstanding contamination in each said bearing assembly comprises a continuous greasing apparatus operably and fixedly attached to bearing elements within each said bearing assembly which continuously and effectively circulate fresh greasing medium into and about said bearing elements, to further preclude the inadvertent contamination, corrosion and undesired creation of excess friction about said rotating bearing elements by constantly greasing same, while further flushing out traces of migrating waste particles and disinfectant solution reaching said rotating elements.

21. The invention according to claim 15 in which said rotary hammermill motor means are operably connected to said primary rotating member within the hammermill apparatus housing through quick release coupling apparatus means which automatically releases said motor means from connection with said primary rotating member upon the occurrence of a torque limiting jam;

said torque limiting jam situation being sensed to activate said quick release coupling through torque sensing apparatus operably communicating with the hammermill apparatus,     said quick release coupling disconnecting said motor means from said hammermill apparatus upon the occurrence of a jam and controlling, automatically, the winding down of the otherwise free riding motor means after such disconnection;

said quick release coupling further including warning means for notifying the operator of said waste disposal system of the occurrence of said hammermill motor means disconnection and wind down.

22. The invention according to claim 1 in which said hammermill transmission means comprises a substantially sealed chute assembly in operable and sealed communication with a hammermill housing operably surrounding the hammermill portion of said rotary hammermill means so as to communicate with the bottom end of said hammermill housing at said first end of said hammermill transmission means,     said hammermill transmission means communicating with said liquid solid particle separation means at said second end.

23. The invention according to claim 1 in which said liquid solid particle separation means comprises;

a substantially sealed particle separator housing means operably attached, in sealed fashion, to the second end of said hammermill transmission means;

particle separator entry means immediately adjacent the second end of said hammermill transmission means through which said disintegrated particles of solid waste and said enveloping-impregnating disinfectant liquid jointly enter said liquid solid particle separation means for separation therebetween;

continuous conveyor sieve means operably positioned immediately adjacent said particle separator entry means for collecting said solid particle—liquid solution therefrom and for separating said disinfectant liquid from said solid waste particles;

said conveyor sieve comprising a substantially continuous looped conveyor element formed by a plurality of interlocking articulated separator belt components;

each said separator belt component including means for attachment to immediately adjacent equivalently constructed separator belt components, a substantially planar surface for supporting said solid waste particles and a plurality of slotted apertures through which said disinfectant liquid may pass towards collection adjacent said liquid evacuation means;

said conveyor sieve powered by separator belt motor means to collect said particle-liquid solution on a continuous basis from said hammermill transmission means;

said conveyor sieve further positioned in a substantially upwardly inclined orientation to deliver said solid waste particles to said solid particle evacuation means and direct the flow of said separated disinfectant liquid to said liquid evacuation means for subsequent independent disposal of same, respectively.

24. The invention according to claim 23 in which each of said separator belt component is possessed of said slotted apertures of a size capable of releasing the majority of disinfectant liquid mixed with said solid waste particles thereupon, while incapable of releasing any substantial volumes of solid waste particles therethrough so as to substantially direct most of said solid waste particles to said solid waste particle evacuation means.

25. The invention according to claim 24 in which said liquid-solid particle separation means further includes;

routing plate means positioned between the upper and lower portions of said substantially continuous conveyor sieve means;

said routing plate serving to direct both said separated disinfectant liquid and particles small enough to pass through said slotted apertures in said separator belt components away from the back side of the lower portion of said conveyor sieve to a position proximate to said liquid evacuation means,     said liquid-solid particle separation means further including conveyor sieve shoulder regions immediately proximate to the longitudinal edges of said conveyor sieve with a brush element positioned operably adjacent said longitudinal edges to further route said solid waste particles towards said solid-waste particle evacuation means;

said liquid-solid particle separation means including scraper means operably positioned immediately proximate said conveyor sieve and said solid waste evacuation means to direct said solid particles from said conveyor sieve into said solid waste evacuation means.

26. The invention according to claim 18 in which said outgoing flush conduits emanating from said bearing spacers are directed for routing said flushing fluid and any associated solid waste particles and disinfectant into said liquid-solid particle separation means for treatment therewithin.

27. The invention according to claim 1 in which said solid waste particle evacuation means has placement detection means operably associated therewith;

said detection means serving to deactivate operation of said liquid-solid particle separation means when said solid waste particle evacuation means is out of position.

28. The invention according to claim 1 in which said liquid evacuation means includes evacuation filter means to preclude the undesired evacuation of accumulated solid waste particles directly through said liquid evacuation means.

29. The invention according to claim 1 in which said system vacuum ventilation means comprises an operably connected series of respective housings about said waste delivery means, preliminary waste processing means, hammermill means and liquid solid separation means, together with said fragment solution channeling means, said hammermill solution transmission means and said one or more slitted draped curtains co-operating to form a substantially sealed uni-directional ventilation circuit,     said ventilation circuit being attached at said liquid-solid waste separation means to fan exhaust means for circulating air within said ventilation circuit in said one direction, through and out from same, said rotary hammermill means further acting as supplemental exhaust means to augment the uni-directional exhausting of potentially bacteria-laden air therethrough, at an exhaust rate less than that of said fan exhaust means, to preclude the forced release of airborne contaminants emanating from said rotary hammermill means, said air within said ventilation circuit being directed from said system input means towards said liquid solid separation means and, in turn, through and out said fan exhaust means.

30. The invention according to claim 29 in which said fan exhaust means comprises;

two or more independent ventilation circuit extension means operably attached, in substantially sealed affixation, to said solid-liquid particle separation means housing for channeling said air within said circuit therefrom;

filtering means operably associated with each of said two or more independent ventilation circuit extension means to filter mists, vapors, waste particles, and bacteria from said air prior to release therefrom;

a blower apparatus operably associated with each of said two or more independent ventilation circuit extension means for creating said uni-directional flow of said air, for driving same through each said filtering means and for ultimately discharging said filtered air from said waste disposal system.

31. The invention according to claim 30 in which each said filtering means includes a plurality of filtering media to filter said mists, vapors, waste particles and bacteria in said air, said plurality of media including hoghair, polyester, pleated and hepa filtering media to effectively filter said air, prior to release of same from said waste disposal system.

32. The invention according to claim 31 in which each said filtering means includes filter monitoring detectors to disclose the occurrence of an overly saturated filtering media element to an operator of said waste disposal system.

33. The invention according to claim 1 in which said system switching control means includes computer controlled switching and sequencing apparata;

said computer controlled switching and sequencing apparata including monitor means with diagnostic means to disclose switching control sequencing operations and problems as they occur and including indicia output means for disclosure of said diagnostic messages.

34. The invention according to claim 33 in which said system switching control means further includes a remote test switching apparatus capable of being physically relocated to any position along said waste disposal system to enable the remote, isolated testing of any structural components thereof by one operator while permitting simultaneous viewing of the results of said switch testing.

35. The waste disposal system of claim 1 in which the invention further comprises elastomeric mounting means operably interposed among the supporting structures for one or more of said waste delivery means, preliminary waste processing means, rotary hammermill means, liquid-solid particle separation means, system vacuum ventilation means and system switching control means, to isolate and effectively reduce the extent of vibration and noise emanating from same.

36. The waste disposal system of claim 1 in which the invention further comprises;

component corrosion control means for spraying onto and through one or more of said waste delivery means, said disinfectant spray means, said preliminary waste processing means, said fragment solution channeling means, said rotary hammermill means and said hammermill solution transmission means, a corrosion preventive coating means when said system is not being used to treat and dispose of infectious waste articles.

37. The invention according to claim 36 in which said component corrosion control means includes said disinfectant spray means for emission of said corrosion preventive coating therefrom, said corrosion preventive coating comprising a plurality of solutions sprayed upon and through said one or more means, said plurality of solutions including a diluted solution of said disinfecting liquid solution, water, and finally, a solution of water-soluble oil and water for coating thereonto said one or more means of said waste disposal system.

* * * * *